United States Patent
Matsui et al.

(10) Patent No.: US 7,355,172 B2
(45) Date of Patent: Apr. 8, 2008

(54) LIQUID CHEROMATOGRAPHY/MASS SPECTROMETRY APPARATUS

(75) Inventors: Mayumi Matsui, Kyoto (JP); Hiroaki Waki, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 367 days.

(21) Appl. No.: 11/287,289

(22) Filed: Nov. 28, 2005

(65) Prior Publication Data

US 2006/0118713 A1    Jun. 8, 2006

(30) Foreign Application Priority Data

Dec. 2, 2004    (JP)    ............................. 2004-349386

(51) Int. Cl.
*B01D 59/44* (2006.01)
(52) U.S. Cl. ...................... 250/288; 250/284; 250/293; 204/600; 204/501; 422/63; 366/341
(58) Field of Classification Search .................... None
See application file for complete search history.

(56) References Cited

U.S. PATENT DOCUMENTS

2007/0045117 A1* 3/2007 Pamula et al. .............. 204/600

* cited by examiner

*Primary Examiner*—Jack Berman
*Assistant Examiner*—Zia R. Hashmi
(74) *Attorney, Agent, or Firm*—Manabu Kanesaka

(57) ABSTRACT

A liquid chromatography/mass spectrometry apparatus combines a chromatograph having a liquid delivery part for delivering mixed multiple solvents, and a mass spectrometer having an ionization part for spraying and ionizing. The apparatus has a storing part for storing a relationship between a mixture ratio of the multiple solvents in the liquid delivery part and an optimal or nearly optimal voltage applied to the ionization part, a ratio information acquiring part for computing the mixture ratio over time, a voltage value computing part for computing the optimal or nearly optimal applied voltage at any point, and a voltage controlling part for changing the voltage applied to the ionization part over time. By virtue of the ability to adjust the applied voltage during analysis, the ionization efficiency is always high, and the analysis can be performed with high sensitivity for all of the multiple components in the liquid sample.

9 Claims, 4 Drawing Sheets

Case when applied voltage is too low

Case when applied voltage is too high

LIQUID CHEROMATOGRAPHY/MASS SPECTROMETRY APPARATUS

BACKGROUND OF THE INVENTION AND RELATED ART STATEMENT

The present invention relates to a liquid chromatography/mass spectrometry apparatus. More specifically, it relates to a liquid chromatography/mass spectrometry apparatus which combines a liquid chromatograph having a liquid delivery part for performing gradient delivery with mixed multiple solvents, and a mass spectrometry device having an atmospheric pressure ionization interface for ionizing sample components by spraying a liquid sample in a roughly atmospheric-pressure atmosphere.

As one analytical means of a liquid chromatograph, there is the gradient delivery method. In this method, multiple solvents having different natures, for example, water and organic solvent, are mixed. The mobile phase liquid is delivered to the column while changing the ratio of the mixture over the passage of time, and it is particularly useful for performing separation into components of samples containing multiple components.

A liquid chromatography/mass spectrometry apparatus (abbreviated below as "LC/MS"), which uses a mass spectrometry device as a detector for such a liquid chromatograph for performing gradient delivery, is known. See, for example, Japanese Unexamined Patent Publication No. H11-326302.

Generally in an LC/MS, an atmospheric-pressure ionization interface is used in order to generate gaseous ions from component molecules in the elution from the column. As representatives of atmospheric-pressure ionization interfaces, there are electro-spray ionization interface (ESI) and atmospheric-pressure chemical ionization interface (APCI), and the like. Both of these have a nozzle for spraying the elution from the column into a roughly atmospheric-pressure atmosphere.

In ESI, a biased charge is applied to a liquid sample when spraying the sample. Making the droplets microscopic is promoted by coulomb repulsion within the sprayed droplets, and in that process the object components within the droplets are ionized.

On the other hand, in APCI, an electrostatic electrode is placed in front of the nozzle, and the object components are ionized by chemically reacting solvent gas ions generated by the corona discharge with the microscopic droplets.

In either case, in such an ionization interface, the spray state of the droplets from the nozzle greatly influences the ionization efficiency, and the value of the applied voltage, which is one of the factors determining the spray state, is one important parameter. However, in the conventional LC/MS, it is common that the applied voltage is fixed at a voltage thought to be nearly optimal.

In an LC/MS for performing the above-mentioned gradient delivery, the MS operating condition uses an optimal value obtained when adjusted under a water/organic solvent condition at a certain mixture ratio. Meanwhile, it is often the case that the optimal value of the applied voltage is provided in advance by the device manufacturer for each device type. But because this voltage value can be changed by the user, for example, in the case when a component eluted under a condition of high organic solvent ratio is important, it is naturally proper to use an optimal value obtained under a mobile phase condition of high organic solvent ratio.

For example, in the case when using ESI as the ionization interface and the MS operating condition is automatically adjusted in the above-described manner, a fixed voltage is applied to the nozzle of the ionization part during analysis by gradient delivery. However, because the spray state of the liquid sample from the nozzle is also dependent on various properties of the mobile phase liquid, for example polarity, viscosity, and the like, it is subject to the influence not only of the type of solvent, but also its mixture ratio, and the like.

Therefore, when the mixture ratio of the solvent changes over the passage of time by gradient delivery, even if the ionization efficiency of the ionization interface was optimal at a certain time (or time period) during analysis, it does not become optimal at other time periods, and at those times, the detection sensitivity also is lowered. As a result, there is a problem that analysis cannot be performed with the highest, or nearly highest, detection sensitivity for all of the multiple components contained in the sample. Thus, one is forced to sacrifice sensitivity when analyzing several components.

It is also often the case that an issue such as that described above does not become so significant a problem with an ESI having a comparatively high flow volume, which is commonly used. As a matter of fact, in nano-ESI, which recently has been widely used in the biochemical field and the like, because the flow volume is as little as 1/100~1/1000 of the conventional volume, a problem such as that described above appears very prominently. Therefore, in extreme cases, it may also be that several of the multiple components contained in a sample cannot be substantially analyzed.

The present invention was created in consideration of the above-described problems. An object of the invention, therefore, is to provide a liquid chromatography/mass spectrometry apparatus in which the ionization efficiency of the ionization interface can always be maintained at a high level.

Another object of the invention is to provide a liquid chromatography/mass spectrometry apparatus in which high-sensitivity analysis of multiple components can be performed, even in the case where the mixture ratio of the solvent changes gradually over the passage of time by gradient delivery.

Further objects and advantages, of the invention will be apparent from the following description of the invention.

SUMMARY OF THE INVENTION

To attain the aforementioned objects, a liquid chromatography/mass spectrometry apparatus according to the present invention is configured as follows.

In a first embodiment of the invention, a liquid chromatography/mass spectrometry apparatus combines a liquid chromatograph having a liquid delivery part for performing gradient delivery with mixed multiple solvents, and a mass spectrometry device having an ionization part for spraying and ionizing in a roughly atmospheric-pressure atmosphere a liquid sample separated into components by that liquid chromatograph.

The apparatus includes a storing means for storing a corresponding relationship between a mixture ratio of multiple solvents in the liquid delivery part and an optimal or nearly optimal applied voltage to the ionization part; a ratio information acquiring means for computing a mixture ratio of multiple solvents in the liquid delivery part over the passage of time during analysis; a computing means for computing an optimal or nearly optimal applied voltage at each point in time during analysis based on a mixture ratio obtained by the ratio information acquiring means while referring to information stored in the storing means; and a voltage controlling means for changing the applied voltage to the ionization part over the passage of time in accordance with a result from the computing means.

In the liquid chromatography/mass spectrometry apparatus according to the present invention, at a suitable point in time in advance of analysis of the object sample, the relationship between the mixture ratio of the multiple solvents used for the analysis, and the applied voltage of such nature that the detection sensitivity of the mass spectrometry device reaches an optimal or nearly optimal state is experimentally investigated. The results of the investigation are stored in the storing means as a relational equation or a table, or the like.

Therefore, in another embodiment of the present invention, the apparatus further includes an information creating means for performing analysis of a prescribed sample. The information creating means performs the analysis by setting the applied voltage to the ionization part in multiple stages when the mixture ratio of multiple solvents from the liquid delivery part is set to a certain state. This determines an optimal or nearly optimal voltage at the mixture ratio, and sets the mixture ratio in multiple stages to obtain an optimal voltage for each stage. The information creating means uses that information to create information to store in the information storing means.

At that time, since it is impossible to actually investigate the relationships between all mixture ratios and optimal applied voltages, one should seek an approximate relationship in order to obtain the optimal or nearly optimal applied voltage by investigating the optimal applied voltage for a suitable mixture ratio. That is, one can obtain the optimal or nearly optimal applied voltage by investigating to the extent of several points, for example, and then performing interpolation processing, or the like, for mixture ratios not actually measured.

During analysis of the object sample by gradient delivery, the ratio information acquiring means computes the change of mixture ratio of the solution over the passage of time from a gradient profile, or the like, for example, for controlling the operation of the liquid delivery part.

The computing means computes the above information stored in the storing means and derives the optimal voltage corresponding to the computed mixture ratio.

Also, the voltage controlling means changes the applied voltage to the ionization part in accordance with the derived optimal applied voltage. By this, as the mixture ratio of the solvent changes following the gradient profile in the liquid delivery part, the applied voltage to the ionization part also is adjusted, so that the ionization efficiency reaches an optimal, or nearly optimal, state.

According to one embodiment of the present invention, the apparatus is configured such that the ionization part performs nano-electro-spray ionization, and the applied voltage is applied to the tip of a nozzle for spraying droplets of liquid sample.

Thus, with the liquid chromatography/mass spectrometry apparatus according to the present invention, even when the mixture ratio of the solvent changes gradually over the passage of time by gradient delivery, the ionization efficiency of the ionization interface can always be maintained at a high level.

Furthermore, the ions can be detected with high sensitivity over almost the entire time band of analysis.

As a result, the analysis can be performed with high sensitivity for all components without sacrificing the sensitivity for several of the multiple components contained in the sample.

BRIEF DESCRIPTION OF THE DRAWINGS

FIGS. 2(a), 2(b), and 2(c) illustrate possible ionization interfaces of the LC/MS according to the first embodiment of the present invention, wherein FIG. 2(a) illustrates an ordinary ESI ionization interface; FIG. 2(b) illustrates a nano-ESI ionization interface; and FIG. 2(c) illustrates an APCI ionization interface.

DETAILED DESCRIPTION OF THE PREFERRED EMBODIMENTS

In the description below, embodiments of the present invention are explained with reference to the drawings that depict an LC/MS.

Figure 1:
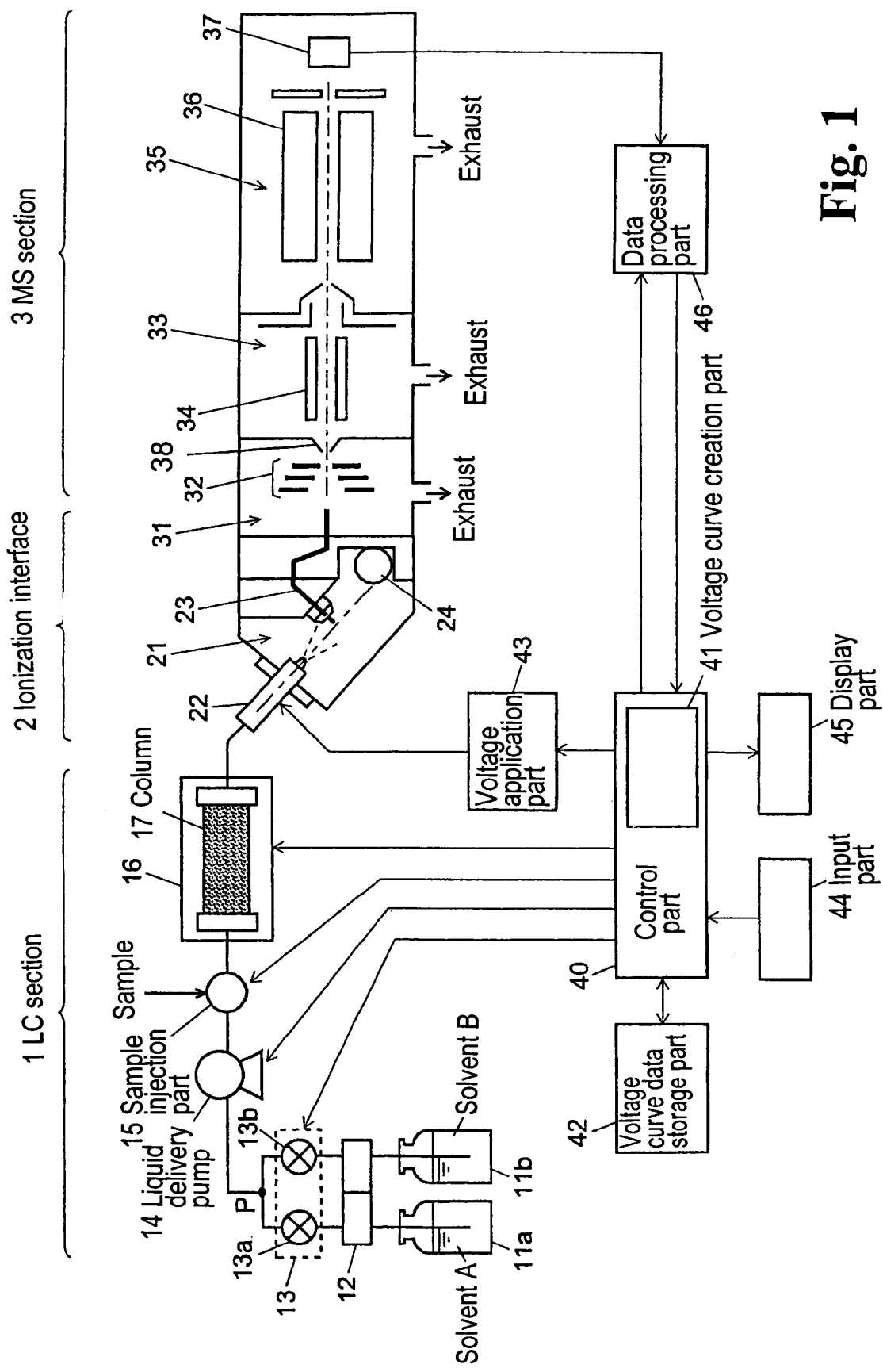
FIG. 1 is a schematic diagram of the components of an LC/MS according to a first embodiment of the present invention.

FIG. 1 is a schematic diagram of the essential components of an LC/MS according to one embodiment of the present invention. The LC/MS depicted is an example of one that performs analysis of a two-liquid gradient in which the composition and properties of the mobile phase liquid are changed by mixing two kinds of solvents. But, of course, it can also be applied to an LC/MS that performs gradient delivery in which three or more kinds of solvents are mixed.

The LC/MS according to one embodiment of the present invention includes generally a liquid chromatography section (LC section) 1 for separating components in a liquid sample, an ionization interface 2 for generating gaseous ions from component molecules in the separated liquid sample, and a mass spectrometry section (MS section) 3 for detecting the sample ions by separating them in accordance with the mass number.

The LC section 1 is a two-liquid low-pressure gradient elution device, in which respectively different solvents A and B are received in two containers (reservoirs) 11a and 11b. On the liquid supply channels from the containers 11a and 11b, there are provided a two-channel type degassing part 12 for removing gas present in dissolved form in the solvents, and a valve 13. The valves 13a and 13b are valves for adjusting the mixture ratios of the two solvents A and B by controlling the respective degrees of valve opening, and the liquid supply channels of the two solvents A and B merge at a point (mixing point) P on the outlet side of these valves 13a and 13b. From this point P, the two solvents A and B flow as a mobile phase that is mixed at a prescribed ratio.

The suction operation of the mobile phase is performed by a liquid delivery pump 14 such as a plunger pump. The mobile phase liquid is delivered in a roughly constant flow volume to a column 17 by means of a sample injection part 15.

In the sample injection part 15, the sample is injected into the flow of the mobile phase liquid at a prescribed timing by an injector valve, or the like.

The injected sample is delivered to the column 17 riding on the flow of the mobile phase liquid. The sample is separated into its respective components while passing through the column 17, and they are respectively eluted from the column 17 over time, and arrive at the ionization interface 2.

The column 17 is housed inside a constant temperature tank 16, and is maintained at a prescribed temperature throughout the analysis. However, in the case of ESI, there is a type of apparatus in which the column and a spray nozzle (to be described below) are integrated. In that case, the constant temperature tank 16 can be omitted.

In FIG. 1, the ionization interface 2 is a nano-ESI interface, and the tip of an ionization, probe 22 connected, to the end of the column 17 is placed protruding inside an ionization chamber 21 which is a nearly atmospheric-pressure atmosphere. An inlet opening of a desolvating pipe 23 for transporting the ions to the later stage is provided in front of the tip of the ionization probe. A drain 24 for discharging non-gasified solvent is placed in front of the desolvating pipe 23. The central axis of the inlet opening of the desolvating pipe 23 intersects diagonally (almost orthogonally) to the central axis of the atmosphere from the tip of the ionization probe 22, whereby the large droplets in which the solvent is not sufficiently gasified are prevented from flowing into the desolvating pipe.

In the MS section 3, a first intermediate vacuum chamber 31 and a second intermediate vacuum chamber 33 respectively separated by a dividing wall are provided between a mass spectrometry chamber 35 and the above ionization chamber 21. A quadrupole filter 36 and a detector 37 as a mass spectrometry part are provided inside the mass spectrometry chamber 35, and first and second ion lenses 32 and 34 are placed respectively inside the first and second intermediate chambers 31 and 33, being located midway therein.

The space between the ionization chamber 21 and the first intermediate vacuum chamber 31 is communicated by way of the above-described desolvating pipe 23, and the space between the first intermediate vacuum chamber 31 and the second intermediate vacuum chamber 33 is communicated by means of a conically-shaped skimmer 38 having a very small diameter pass-through hole at the vertex.

As described above, the inside of the ionization chamber 21 is a nearly atmospheric-pressure atmosphere. The inside of the first intermediate vacuum chamber 31 is evacuated to about $10^2$ [Pa], the inside of the second vacuum chamber 33 is evacuated to about $10^{-1}$~$10^{-2}$ [Pa], and the inside of the mass spectrometry chamber 35 is evacuated to a high vacuum state of about $10^{-3}$~$10^{-4}$ [Pa]. Thus by configuring the apparatus as a multistage differential exhaust system that raises the degree of vacuum in stages, with an ionization chamber 21, first intermediate vacuum chamber 31, second intermediate vacuum chamber 33, and mass spectrometry chamber 35, the high degree of vacuum inside the mass spectrometry chamber 35 is maintained.

To generally explain the operation of the ionization interface 2 and the MS section 3, as described above, the sample liquid eluted from the column 17 is sprayed inside the ionization chamber 21 from the tip of the ionization probe 22, and the molecules of the sample within the spray flow are ionized. The generated ions are drawn into the desolvating pipe 23, together with microscopic droplets not yet ionized, by differential pressure between the ionization chamber 21 and the first intermediate vacuum chamber 31.

The first ion lens 32 helps the drawing-in of the ions via the desolvating pipe 23 by its magnetic field, and also causes the ions to converge near the pass-through hole of the skimmer 38.

The ions introduced into the second intermediate vacuum chamber 33 through the pass-through hole of the skimmer 38 are made to converge, and are accelerated by the second ion lens 34. The ions are then sent to the mass spectrometry chamber 35.

In the mass spectrometry chamber 35, only the ions having a specific mass number escape through the space in the long axial direction of the quadrupole filter 36, reach the detector 37, and are detected as ion current. This detection signal is sent to a data processing part 46.

In the data processing part 46, various kinds of graphs such as mass spectra and mass chromatograms are created. In addition, prescribed data processing such as qualitative analysis and quantitative analysis is executed.

A control part 40, to which are connected an input part 44 and a display part 45, has the function of administering control of the overall operations of the present apparatus, and in particular it controls the applied voltage to the ionization probe 22 by means of a voltage application part 43. Also, as a characteristic configuration of the present embodiment, the control part 40 includes a voltage curve creation part 41 as a functional block, and a voltage curve data storage part 42 is connected to the control part 40. The operations of these are described in detail below. Usually, the control part 40, voltage curve data storage part 42, data processing part 46, and the like, are embodied by control and processing programs installed on a personal computer.

In the LC/MS of the embodiment described herein, any of ESI, nano-ESI, or APCI can be performed selectively by replacing the ionization probe 22. This point is explained using FIG. 2.

Figure 2A:
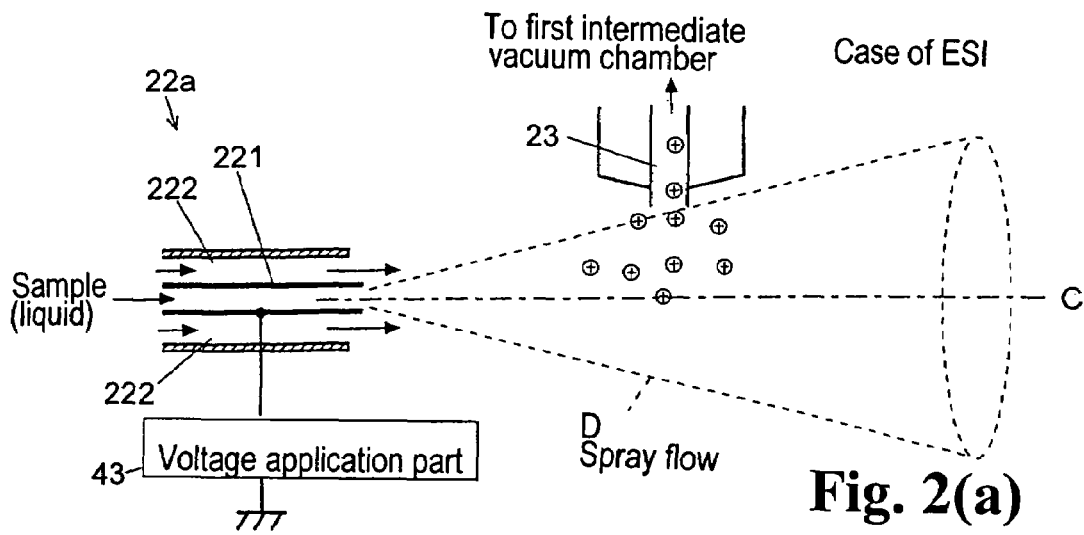

In the case of ordinary ESI, as shown in FIG. 2(a), the ionization probe 22a for spraying the sample liquid has a nozzle 221 to which the sample liquid is supplied, and a nebulized gas pipe 222 which is placed coaxially with the nozzle 221 and in a manner so as to surround it as an outer pipe. High voltage direct current in the range of several kV is applied by the voltage application part 43 to the nozzle 221 itself, or to a metal pipe (not illustrated) which is provided on its perimeter. By the influence of the electric field produced by this voltage, the sample liquid flowing up to the nozzle 221 is bias charged, and in that state, it is sprayed out as microscopic droplets with the help of nebulized gas (usually $N_2$ gas) sprayed from the nebulized gas pipe 222.

The sprayed-out microscopic droplets come in contact with dry nitrogen gas, for example, which is sprayed from the perimeter of the desolvating pipe 23. The mobile phase, or solvent, in the droplets rapidly evaporates, and the size of the droplets becomes smaller. As a result, the droplets can be finely split by the coulomb repulsion of the applied charge, and in that process, gaseous ions originating from the sample molecules are produced.

The nozzle 221 sprays the sample liquid in a direction nearly orthogonal to the central axis of the inlet opening of the desolvating pipe 23, and the spray flow D progresses while widening in a nearly conical form. In the course of that progress, sample ions are generated as described above, and the ions are sucked into the desolvating pipe 23 in a state having droplets mixed in.

Figure 2B:
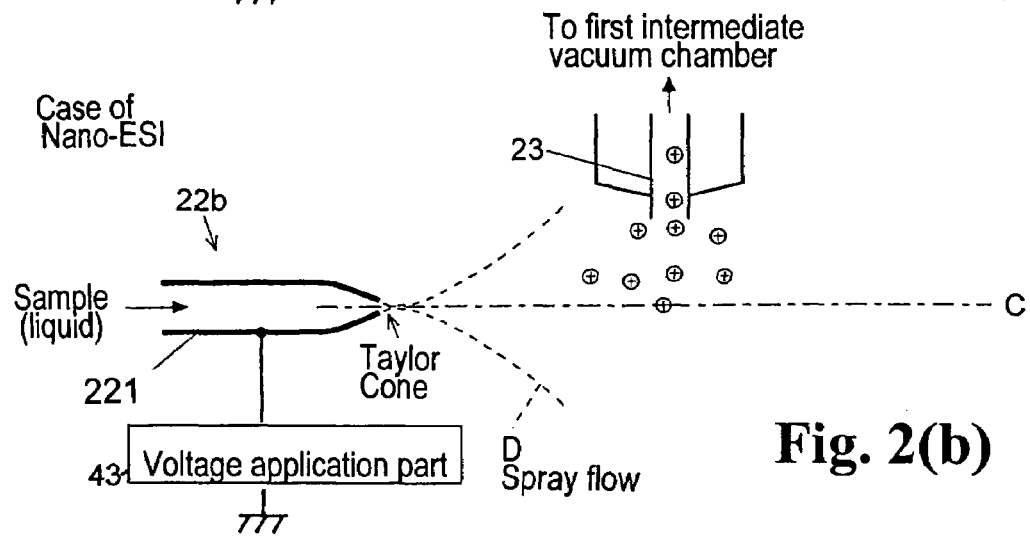

In the case of nano-ESI, as shown in FIG. 2(b), it is basically configured by removing the nebulized gas and dry nitrogen gas from the configuration of the above-described ESI. The tip of the nozzle 221 for spraying the liquid sample is a capillary tube using a glass capillary coated with a metal thin film, or a metal capillary, or the like, and the tip is narrowly constricted. In nano-ESI, because there is no assistance of the spray using nebulized gas, the liquid sample containing a large quantity of homopolar ions, which flows out from the tip of the nozzle 221, is drawn out weakly by the coulomb force, and it forms a conical shape called a Taylor cone. As the charge density becomes higher during the flow of the sample, a coulomb explosion occurs at a critical point, and it widens conically with the generation of ions.

Figure 2C:
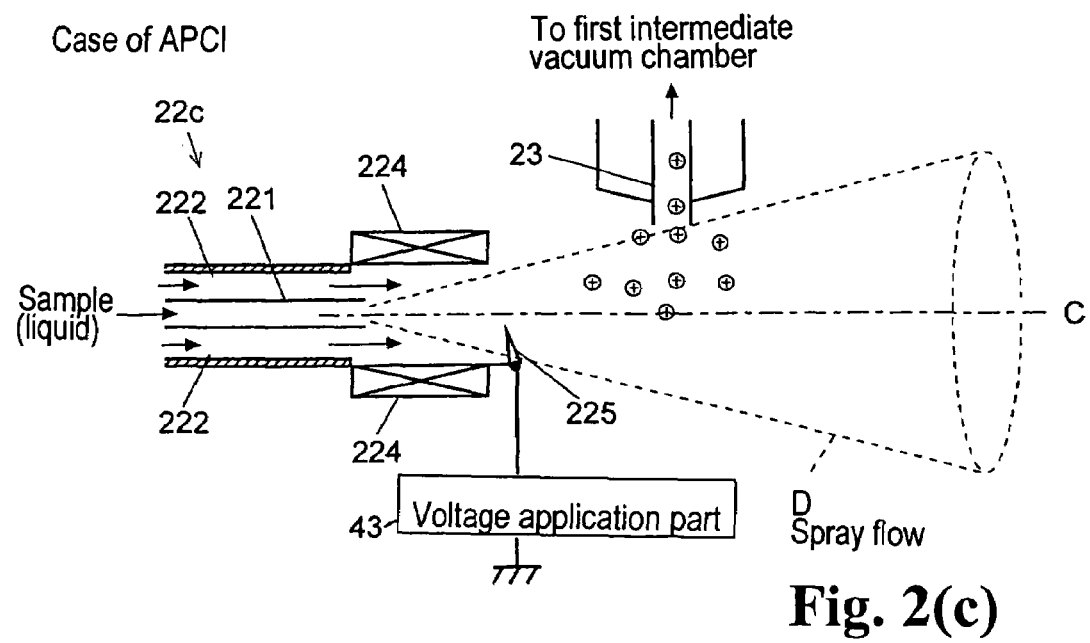

In the case of APCI, as shown in FIG. 2(*c*), an ionization probe 22*c* is used. A heater 224 wound around a space in front of the opening of the nozzle 221, and a needle-shaped discharge electrode 225 provided further in front of that, are integrated on the nozzle 221 and the nebulized gas pipe 222.

The sample liquid reaching the tip of the nozzle 221 (which differs from ESI in that it is not charged) becomes microscopic droplets with the help of the nebulized gas sprayed out from the nebulized gas pipe 222 and is sprayed out as a spray flow D while widening in a roughly conical shape. Since the space in front of it is wound around with a heater 224, the solvent in the droplets is gasified to become solvent gas by the heating of the heater 224. When high voltage is applied in pulses to the discharge electrode 225 from a high voltage source, a corona discharge occurs, and the solvent gas molecules become solvent ions. These solvent ions and the sample molecules in the droplets chemically react, and the sample molecules are ionized to become sample ions.

The spray flow D of sample droplets sprayed from the nozzle 221 depicted in FIGS. 2(*a*)-2(*c*) as being a roughly conical shape is a nearly ideal state. The spray flow D attains such a state when the voltage applied to the ionization probe 22 is adjusted properly. For example, in nano-ESI, when the applied voltage to the nozzle 221 is too low, the coulomb force within the droplets sprayed out does not act sufficiently, and many of the droplets tend to progress in a state of not being made microscopic. As a result, as shown in FIG. 5(*a*), the spray flow D does not widen out greatly in a conical shape, and it becomes a shape such as being sprayed out nearly in a straight line.

Figure 5A:
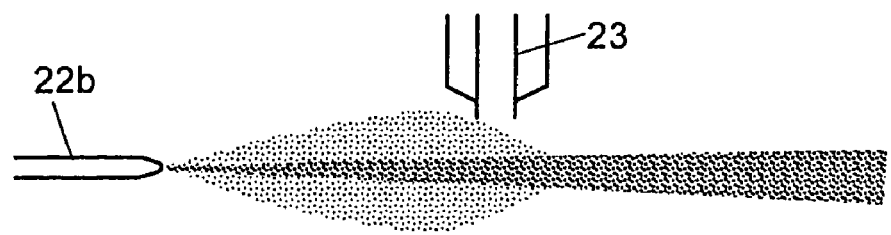
FIGS. 5(a) and 5(b) illustrate the spray states of droplets in cases when the applied voltage to the nozzle is not proper in nano-ESI.
Figure 5B:
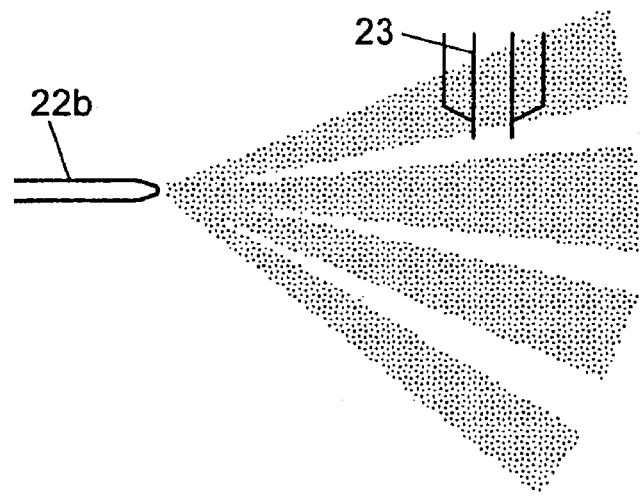

Conversely, when the applied voltage is too high, the spray flow does not become a clean conical shape, and as shown in FIG. 5(*b*), it becomes a shape such as the spray flow flying about in various directions. In either case, because ionization is not performed adequately, the ionization efficiency is lowered.

Because the spray condition of the droplets is also dependent on the nature of the solvent of the sample liquid, i.e., the mobile phase liquid, if the nature of the mobile phase liquid differs, then the optimal applied voltage also differs. Accordingly, if the applied voltage is made constant in gradient analysis, even though the applied voltage becomes optimal at a certain point in time, at other time periods the applied voltage does not become optimal, and the ionization efficiency is thus lowered.

Therefore, in the LC/MS according to the embodiment described herein, by performing characteristic control when performing gradient analysis, the ionization efficiency in the ionization interface 2 is kept in an optimal state. This point is explained in detail below.

First, in advance of analysis of the actual object sample, the corresponding relationship between the mixture ratio of two solvents A and B used in the analysis and the optimal applied voltage is investigated at a suitable time. That relationship is then stored in the storage part 42 as voltage curve data. In the apparatus of the present embodiment, the voltage curve creation part 41 has the function of automatically performing acquisition of the voltage curve data. That is, the user (operator) prepares the solvents A and B in the containers 11*a* and 11*b*, prepares an arbitrary sample (for example a standard sample) as the sample, and gives an instruction to automatically adjust the analytical conditions from the input part 44. As a result, the voltage curve creation part 41 starts preparatory analysis as one process to adjust the various analytical conditions.

In the preparatory analysis, analysis of the sample is performed in a state in which the liquid delivery flow volume in the liquid delivery pump 14 is set to the same value as during analysis, and the degree of opening of the valves 13*a* and 13*b* is set suitably so that it becomes a prescribed mixture ratio. At that time the applied voltage is scanned within a prescribed range to find an applied voltage such that the detection signal by the detector 37 becomes greatest, i.e., the sensitivity becomes optimal.

Figure 3:
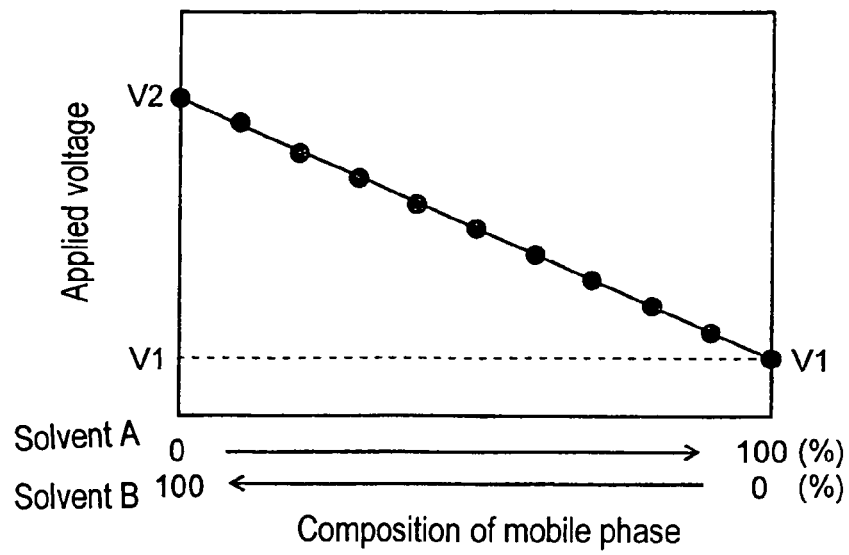
FIG. 3 is a graph showing one example of a voltage curve created in the LC/MS according to the first embodiment of the present invention.

The applied voltage at this time is the optimal applied voltage with which the ionization efficiency in the ionization interface 2 becomes optimal. For example, when solvent A is 0.1% formic acid aqueous solution and solvent B is acetonitrile, the optimal applied voltage is sought respectively for each case when the ratio of solvent B is changed in 10% steps as 0, 10, 20, 30, . . . , 100%. Based on the result of that, the voltage curve creation part 41, for example as shown in FIG. 3, computes an approximation curve of optimal applied voltage when the ratio of solvent B is changed within a range of 0~100%. The data which expresses this approximation curve, for example, by a formula or expresses it in a table format, is voltage curve data. This voltage curve data is stored in the storage part 42. In the automatic adjustment processing of analytical conditions, because various other analytical conditions also are sought, it should be configured such that the voltage curve data is stored as one of the tuning parameters in a tuning file having the data compiled as tuning parameters.

Figure 4A:
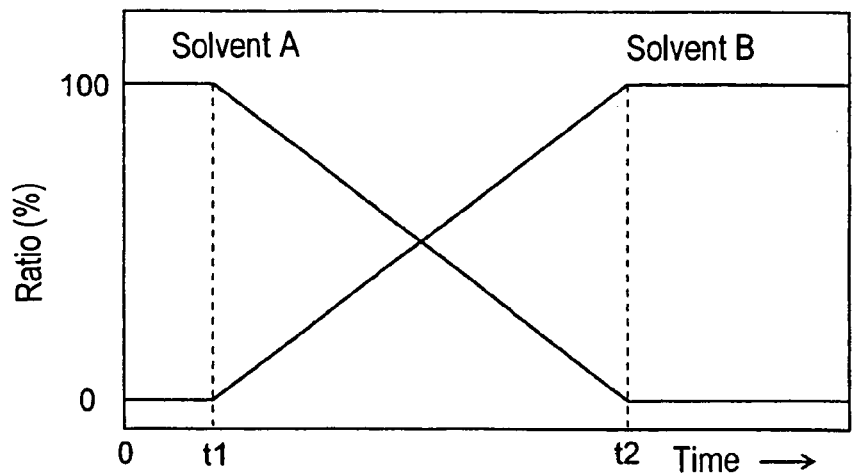
FIGS. 4(a) and 4(b) are graphs showing one example of a gradient profile (FIG. 4(a)) and actual applied voltage change pattern (FIG. 4(b)) in the LC/MS according to the first embodiment of the present invention.
Figure 4B:
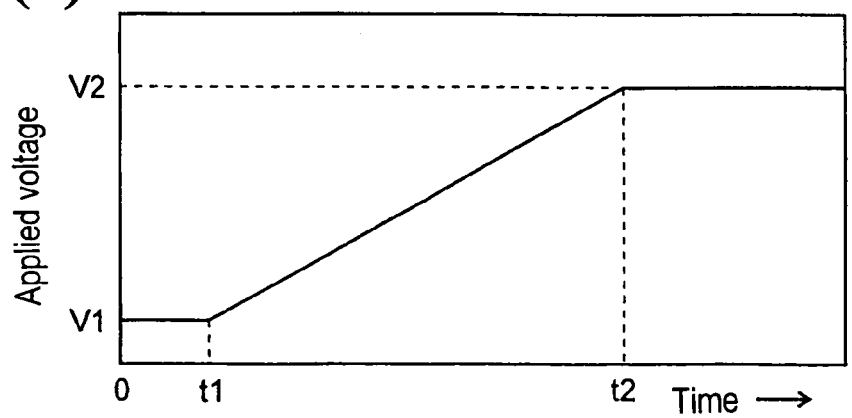

When performing analysis of the object sample, the user sets a gradient profile, for example, as shown in FIG. 4(*a*) from the input part 44, and starts analysis. The gradient profile indicates the target value of the mixture ratio of the mobile phase liquid over the passage of time from the start of analysis.

When the analysis is started, the control part 40 controls the respective degrees of opening of the valves 13*a* and 13*b* following the gradient profile, whereby the object sample is injected by the sample injection part 15 into the flow of the mobile phase having a determined mixture ratio. Also, the control part 40 reads out the voltage curve data stored in the storage part 42, and refers to that voltage curve to seek an optimal applied voltage from the mixture ratio of the mobile phase liquid that can be read from the gradient profile. Also, the control part 40 controls the voltage application part 43 in accordance with the sought optimal applied voltage value, and the voltage is applied to the ionization probe 22 (nozzle 221).

The control part 40 goes on to successively change the optimal applied voltage each time the mixture ratio read from the gradient profile changes over the passage of time. Thus, as shown in FIG. 4(*b*), the applied voltage V1 is maintained until time t1 up to which the state of solvent A: 100%, solvent B: 0% continues, and during the period from time t1 to t2 in which the mixture ratio changes complementarily, it is scanned so that the applied voltage increases from V1 to V2. Also, from time t2 on, the applied voltage is kept at V2 as the state of solvent A: 0%, solvent B: 100% continues.

By such control as is described above, a voltage of a nature such that the spray state of the droplets always is that which is desired is applied to the ionization probe 22. Because of that, a state in which the ionization efficiency is nearly optimal is maintained inside the ionization chamber 21. Consequently, maintaining an analysis state in which the detection sensitivity is also nearly optimal, becomes possible.

In addition to the types of solvents constituting the mobile phase liquid, the voltage curve changes depending also on the flow volume of the mobile phase liquid. Accordingly, it is obvious in the case when the types of solvents are different, but in the case when the type of solvent is the same but the flow rates are different, it is necessary to seek a new voltage curve. Conversely, if a voltage curve in which the type and flow volume of the solvent are the same was acquired in the past, it is possible to perform analysis of the object sample using that voltage curve.

In the embodiment described herein, an embodiment in which the ionization interface 2 is nano-ESI was explained, but the same kind of control can also be applied for ordinary ESI and APCI. However, in the case of APCI (see FIG. 2(*c*)), a major factor governing the ionization efficiency in the ionization interface 2 is the high voltage applied to the discharge electrode 225 for producing the corona discharge. Accordingly, instead of adjusting the high voltage applied to the tip of the nozzle 221 in nano-ESI as described above, in APCI, it should be configured so as to adjust the value of the voltage applied to the discharge electrode 225 in accordance with the mixture ratio of the mobile phase liquid.

The above-described embodiment is but one example of the apparatus according to the present invention. The description is illustrative, and the scope of the invention, including modifications, revisions, and additions thereto, is limited only by the appended claims.

The disclosure of Japanese Patent Application No. 2004-349386 filed on Dec. 2, 2004, is incorporated herein.

What is claimed is:

1. A liquid chromatography/mass spectrometry apparatus, which combines a liquid chromatograph having a liquid delivery part for performing gradient delivery with mixed multiple solvents, and a mass spectrometry device having an ionization part for spraying and ionizing in a roughly atmospheric-pressure atmosphere a liquid sample separated into components by said liquid chromatograph, said apparatus comprising:
   storing means for storing a corresponding relationship between a mixture ratio of said multiple solvents in said liquid delivery part and a substantially optimal voltage applied to said ionization part;
   ratio information acquiring means for computing said mixture ratio of multiple solvents in said liquid delivery part over passage of time during analysis of said sample;
   voltage value computing means for computing said substantially optimal voltage at any point in time during said analysis based on said mixture ratio obtained by said ratio information acquiring means while referring to information stored in said storing means; and
   voltage controlling means for changing said voltage applied to said ionization part over the passage of time in accordance with a computed result from said voltage value computing means.

2. A liquid chromatography/mass spectrometry apparatus according to claim 1, further comprising information creating means for performing said sample analysis by setting said voltage applied to said ionization part in multiple stages when said mixture ratio of multiple solvents is set to a certain state, so as to determine said substantially optimal voltage at said mixture ratio, and to set said mixture ratio in multiple stages so as to obtain an optimal voltage for each stage, and by using said voltages and mixture ratios to create information for storage in said information storing means.

3. A liquid chromatography/mass spectrometry apparatus according to claim 1, wherein said ionization part performs nano-electro-spray ionization, and said voltage is applied to a tip of a nozzle for spraying droplets of said liquid sample.

4. A liquid chromatography/mass spectrometry apparatus according to claim 1, wherein said ionization part performs electro-spray ionization, and said voltage is applied to a body of a nozzle for spraying droplets of said liquid sample.

5. A liquid chromatography/mass spectrometry apparatus according to claim 1, wherein said ionization part performs atmospheric-pressure chemical ionization, and said voltage is applied to a discharge electrode for ionizing solvent gas molecules.

6. A liquid chromatography/mass spectrometry apparatus according to claim 1, wherein said substantially optimal voltage is a voltage at which ionization efficiency in said ionization part becomes optimal for a particular mixture ratio.

7. A liquid chromatography/mass spectrometry apparatus according to claim 1, wherein said voltage controlling means successively changes said optimal voltage each time said mixture ratio changes over the passage of time.

8. A liquid chromatography/mass spectrometry apparatus according to claim 1, wherein said ratio information acquiring means for computing said mixture ratio comprises accounting for types of said multiple solvents.

9. A liquid chromatography/mass spectrometry apparatus according to claim 1, wherein said ratio information acquiring means for computing said mixture ratio comprises accounting for flow rates of said multiple solvents.

* * * * *